United States Patent [19]

Holländer et al.

[11] 4,123,159

[45] Oct. 31, 1978

[54] APPARATUS FOR ANALYZING THE SIZE DISTRIBUTION AND QUANTITY OF SMALL PARTICLES IN AN AEROSOL

[76] Inventors: Werner Holländer, No. 15, Astenbergstrasse, 5949 Westfeld; Josef Schörmann, No. 4, Im Kampe, 5948 Schmallenberg, Grafschaft, both of Fed. Rep. of Germany

[21] Appl. No.: 767,193

[22] Filed: Feb. 9, 1977

[51] Int. Cl.² ........................ G01N 1/00; G01N 15/02
[52] U.S. Cl. ........................................ 356/38; 356/102
[58] Field of Search ................ 356/38, 209, 207, 102; 73/61 R, 432 PS

[56] References Cited

U.S. PATENT DOCUMENTS 3,942,360  3/1976  Wada .................................. 73/61 R

*Primary Examiner*—Conrad J. Clark
*Attorney, Agent, or Firm*—John C. Smith, Jr.

[57] ABSTRACT

An apparatus for analyzing the size distribution and quantity of small particles in an aerosol comprises at least one smooth filter bearing a reflecting coating and means for measuring the change in reflectance due to the deposition of intercepted particles. At least one additional filter contains linear pores extending substantially normal to the filter surface and has a negligible transmission outside the pores. Also realized are means for measuring the change in transmission due to the retention of particles in and around the pores.

6 Claims, 4 Drawing Figures

APPARATUS FOR ANALYZING THE SIZE DISTRIBUTION AND QUANTITY OF SMALL PARTICLES IN AN AEROSOL

BACKGROUND OF THE INVENTION

This invention relates to apparatus for analyzing the size distribution and quantity of small particles in an aerosol.

Compliance with regulations governing maximum emission values, so-called MAK-values, to combat air pollution call for the provision of suitable measuring techniques (local and remote measurements). Local measurement should be simple and capable of being continuously performed for analyzing the particle size distribution in the aerosol, and at least they should be capable of discriminating between coarse and invasive fine pulmonary dusts with the necessary sensitivity.

It is the general practice to make use of instruments based on the light scattering effect of suspensoids, or of centrifuges or filters.

Commercial diffusion measuring instruments are technically complex and they fail to detect very small particles. On the other hand, they generate an electrical signal which is convenient to evaluate.

Centrifuges have very high resolution powers, but the measurement (weighing) requires the collection of a large amount of material and is difficult to perform.

Sampling by means of filters is an easy method, but for the measurement of a precipitate by weighing a large amount of material is likewise required. Moreover, some filters do not discriminate between the precipitated particle sizes.

These known measuring techniques are not therefore capable of meeting all the requirements for solving the contemplated problem.

SUMMARY OF THE INVENTION

It is the object of the present invention to avoid these disadvantages.

To attain this object the present invention provides an apparatus for analyzing the size distribution and quantity of small particles in an aerosol, which comprises at least one smooth filter bearing a reflecting coating, means for measuring the change in reflectance due to the deposition of intercepted particles, at least one additional filter containing linear pores extending substantially normal to the filter surface, said filter having a negligible transmission outside the pores, and means for measuring the change in transmission due to the retention of particles in and around the pores.

Filters which have a good monodispersion of pore sizes, a very smooth surface, not being very thick, and contain pores extending linearly and normal to the filter surface, more particularly that sold under the trademark Nuclepore, have proved advantageous.

The filters which are originally milky translucent are provided on one or both sides with an opaque and/or highly reflecting layer of metal or a dielectric, without however blocking the pores. This can be accomplished for instance by vaporizing in a vacuum, sputtering and like techniques.

The aerosol is then drawn by suction serially in succession through filtering stages provided with filter sheets that have thus been prepared. The disposition of the filters is so arranged that in the first stage the largest particles are retained, that the particles interrupted in the following stages are consecutively smaller, and that in the final stage even the finest floating particles are retained so that all impurities in particle form originally contained in the air (or the gas) are deposited in the several stages. The size discriminating power of the apparatus is determined by the number of filter stages and the uniformity of the pore sizes.

Now it is proposed that the continuous measurement of even the minutest precipitates in the several filter stages should be carried out in one of two ways in which light (whether coherent or monochromatic or natural or polarized or combinations of these forms will depend upon the particular purpose of the measurement) impinges on the side facing the particle stream (or on the other side). These alternatives are:

1. To measure the change in reflectance or in the light diffusing properties of the reflecting surface of the filter sheet caused by the aerosol particles; this method offers itself for medium and large sized particles, i.e., for the leading filter stages.

2. To measure the change in transmission of the filters which have been vaporized on one or both sides in such a way that light can pass through the filter only through the pores extending perpendicularly to the filter surface. Since for aerodynamic reasons the particles deposit themselves primarily around the pore edges, they affect transmission through the pores in a manner suitable for the measurement. Since by collecting a particle each pore loses some of its transmission, the sensitivity of the method is principally dependent upon the proportion of the number of particles retained at the pore edges to the total number of pores present and not upon the total precipitated volume, as is the case in every other method. Hence the apparatus according to the invention is particularly suitable for the measurement of minute air pollution (both regarding size and quantity). This is accentuated by the fact that the measuring effect is best when $d/\lambda$ ($d$ = pore diameter; $\lambda$ = wavelength of light) is small.

The change in the light intensity after reflection and transmission according to 1 and 2 above can be measured by using ordinary semiconductor photodiodes either directly, or by employing the difference method using a reference beam derived from the same light source.

Either a) the difference can be formed electrically with the aid of two diodes and amplifiers or b) the light of both reference and measured beam can be passed through an optical chopper in which case the measuring signal can be obtained in the form of an a.c. voltage from a single diode with one amplifier. The optical chopper functions as follows:

Preceding the detector entry the measuring and reference beams are each passed through a polarizing filter which polarizes them in relatively perpendicular planes. A rotating analyzer following the two polarizers extinguishes and transmits the beams in alternation. The chopped light signal falls on the diode which applies a corresponding electrical signal to the evaluating electronics.

BRIEF DESCRIPTION OF THE DRAWING

The invention will now be described by way of example and with reference to the accompanying schematic drawing, in which.

DESCRIPTION OF THE PREFERRED EMBODIMENTS

Figure 1:
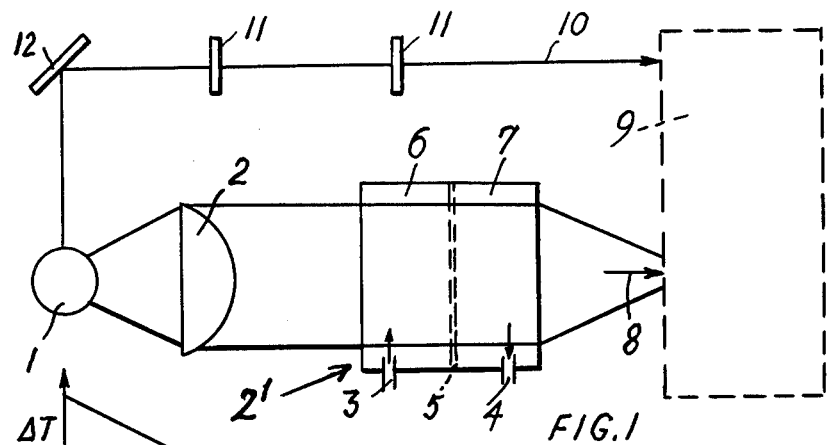
FIG. 1 illustrates the principle underlying the proposed measuring system.

With reference first to FIG. 1 a conventional incandescent lamp 1 and a condenser 2 provide a parallel measuring beam in which the light intensity is substantially uniformly distributed throughout the cross section. In the path of the measuring beam there is provided a transparent airtight measuring cell $2^1$ having an aerosol admission opening 3 and an aerosol outlet opening 4. The measuring cell $2^1$ is internally divided by a filter leaf 5 into two chambers 6 and 7. Light is transmitted only through pores in the filter, the rest of the filter surface having been rendered opaque by a suitable treatment. After having passed through the measuring cell $2^1$ the transmitted light of the measuring beam is collected as at 8 and applied to one input of an electronic system 9. The aerosol enters the measuring cell through the admission opening 3. Owing to the minuteness of the filter pores the particles on the side of the filter facing the lamp 1 are deposited principally around the mouths of the pores. This affects the intensity of the light transmitted by the filter 5. Since normally this change will not be very large, it is determined by a sensitive differential technique as follows: Part of the light of the lamp 1 is diverted for use as a reference beam 10 which after reflection at one or more mirrors 12 is attenuated by light intensity reducing devices 11 of any type, such as crossed polarizing filters, grey wedge, mechanical diaphragms and so forth, until before the measurement begins the reference beam 10 for comparison purposes is of the same intensity as the measuring beam. Since the reference beam 10 maintains a constant intensity throughout the test any intensity difference arising between the measuring beam and the reference beam permits the conclusions to be drawn regarding quantity of intercepted aerosol.

In order to measure the particle size distribution several instruments of the kind illustrated in FIG. 1, fitted with filters having different retention characteristics, must be associated with each other in series.

Figure 2:
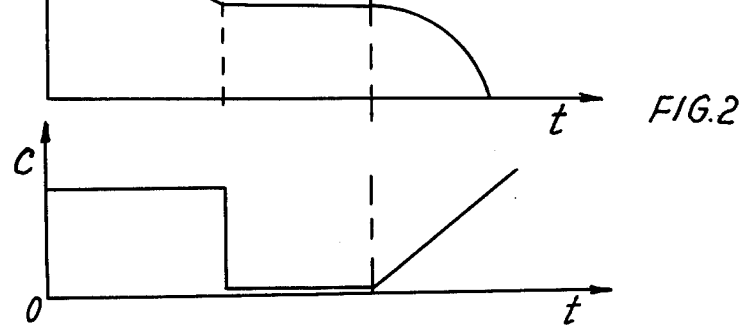
FIG. 2 is a representation of the measuring signals.

Referring now to FIG. 2, and assuming that the aerosol concentration remains constant, the quantity of deposits will be exactly proportional to the filtered aerosol volume and this will in turn be a function of time — always assuming that the operative suction head through the filter also remains constant. Under these conditions the change in transmission $\Delta T$ effected by the filters and measured at the output of the electronic system will be a linear function of time $t$. For instance, if clean air is drawn through the measuring cell there will be no change in transmission. It will therefore be possible to determine the transient aerosol concentration C by differentiating the transmission curve with respect to time. This principle enables the aerosol concentration C to be continuously measured.

Differentiation of the measurement curve $\Delta T$ with respect to $t$ thus gives the concentration of the aerosol — subject to the suction performance through the filter being known and constant. Contrary to other filtration methods the described procedure therefore measures the impurity content continuously.

Figure 3:
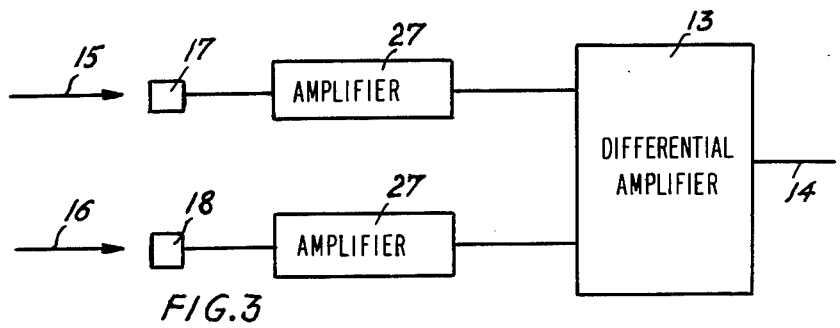
FIG. 3 are electronic circuit arrangements for measuring changes in the transmittance of the filters by the difference method.

The change in transmission $\Delta T$ or the relative intensity change of the measuring beam to the reference beam can in principle be determined in two different ways:

The first is by the difference method illustrated in FIG. 3. Here the two light beams are converted in separate electronic circuits comprising photodiodes 17 and 18 and operational amplifiers 27 into corresponding electrical signals which are compared for the formation of a difference signal. The principle advantage afforded by this system, namely the simplicity of the instrumentation and the absence of mechanically movable parts is offset by one major drawback, namely that every component has a different and unknown electrical drift so that a signal 14 will appear in the output of the differential amplifier 13 even when the light intensities of the reference beam 15 and of the measuring beam 16 are the same. This phenomenon limits the utility of such arrangements when the measurements are to cover long periods of time.

Figure 4:
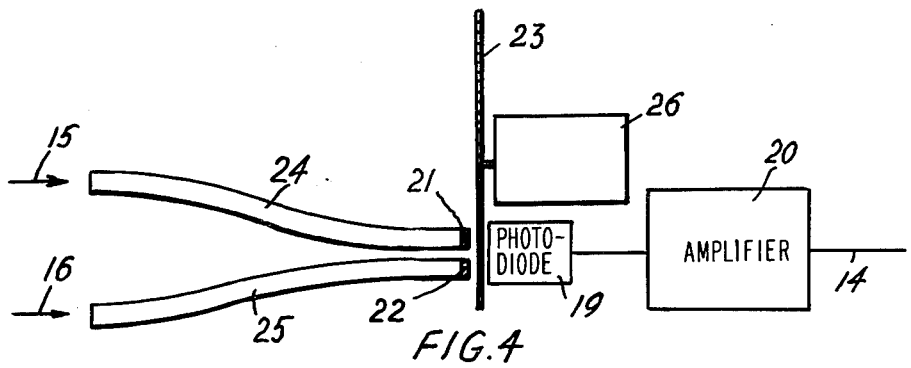
FIG. 4 illustrates the light chopper method.

In the second, i.e., the so-called chopper method, illustrated in FIG. 4 the two beams 15 and 16 are applied in alternation at intervals measured in milliseconds through light conductors 24 and 25 to one single photodiode 19 associated with an amplifier 20. The effect of drift on a difference signal is thereby eliminated and a simple and rugged a.c. amplifier 20 can be used. This is a considerable advantage of the chopper technique. The rapid changeover between the beams is achieved by first polarizing the reference and measuring beams in polarizing filters 21 and 22 so that their respective planes of polarization are relatively perpendicular. By then interposing an analyzer 23 between the polarizers and the photodiode 19 and rotating the analyzer by means of a motor 26, the beams will be allowed to pass through to the diode 19 in alternation at 90° intervals in the course of each revolution.

In intermediate positions of the rotating analyzer 23 components of both beams will be transmitted so that there will be a continuous overlap of sine-wave characteristic between the two beams.

The advantages of the proposed arrangement compared with conventional mechanical chopper devices are:

1. that the rotating component is a homogeneous component which will therefore run with the utmost smoothness without any tendency to imbalance, and
2. that in many applications the sine-shaped output signal and the continuous overlap between the two beams is desirable.

The invention may be embodied in other specific forms without departing from the spirit or essential characteristics thereof. The embodiments are therefore to be considered in all respects as illustrative and not restricitive.

What we claim is:

1. An apparatus for analyzing the size distribution and quantity of small particles in an aerosol, which comprises at least one filter containing linear pores extending substantially normal to the filter surface, said filter being substantially opaque outside the pores, means for directing light onto said filter surface on one side thereof, and means for measuring the change in transmission of said light through said pores due to the retention of particles in and around the pores.

2. An apparatus according to claim 1, wherein said substantially opaque filter includes a metal coating on at least one side thereof which coating does not block said pores in said filter.

3. An apparatus according to claim 1, wherein the filters have been vaporized with an opaque material in such a way that the pores remain uncovered.

4. An apparatus according to claim 1, wherein said measuring means is adapted to continuously perform measurements.

5. An apparatus according to claim 2, wherein said coating is highly reflective.

6. An apparatus according to claim 1, wherein said substantially opaque filter includes a dielectric coating on at least one side thereof which coating does not block said pores in said filter.

* * * * *